United States Patent
Walter et al.

(10) Patent No.: US 7,209,536 B2
(45) Date of Patent: Apr. 24, 2007

(54) CT COLONOGRAPHY SYSTEM

(75) Inventors: Deborah Walter, Burnt Hills, NY (US); Kelly L. Piacsek, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 89 days.

(21) Appl. No.: 10/904,630

(22) Filed: Nov. 19, 2004

(65) Prior Publication Data

US 2006/0109953 A1 May 25, 2006

(51) Int. Cl.
*H05G 1/60* (2006.01)

(52) U.S. Cl. .............................................. 378/5; 378/9

(58) Field of Classification Search .................. 378/5, 378/49, 82, 83, 56, 6–10, 15–20, 48; 600/420, 600/431
See application file for complete search history.

(56) References Cited

U.S. PATENT DOCUMENTS

| | | | |
|---|---|---|---|
| 5,400,378 A | | 3/1995 | Toth |
| 5,485,492 A | * | 1/1996 | Pelc .............................. 378/5 |
| 5,611,342 A | * | 3/1997 | Widder ....................... 600/431 |
| 6,231,834 B1 | * | 5/2001 | Unger et al. ............... 424/9.51 |
| 6,285,740 B1 | * | 9/2001 | Seely et al. ................. 378/98.9 |
| 6,418,189 B1 | * | 7/2002 | Schafer ........................ 378/57 |
| 6,480,565 B1 | * | 11/2002 | Ning ............................. 378/37 |
| 6,671,540 B1 | * | 12/2003 | Hochman .................... 600/431 |
| 2002/0097321 A1 | | 7/2002 | Zalis ............................. 348/65 |
| 2003/0023163 A1 | | 1/2003 | Johnson et al. ............. 600/431 |
| 2003/0113267 A1 | | 6/2003 | Knopp et al. ............. 424/9.363 |
| 2003/0147502 A1 | * | 8/2003 | Heismann et al. .......... 378/156 |
| 2003/0223627 A1 | * | 12/2003 | Yoshida et al. ............. 382/128 |
| 2004/0066881 A1 | * | 4/2004 | Reddy et al. .................. 378/5 |
| 2004/0101086 A1 | * | 5/2004 | Sabol et al. ................... 375/4 |
| 2004/0101089 A1 | * | 5/2004 | Karau et al. ................... 378/4 |
| 2004/0136491 A1 | | 7/2004 | Iatrou et al. .................... 378/4 |
| 2004/0184574 A1 | * | 9/2004 | Wu et al. ....................... 378/5 |
| 2004/0264627 A1 | | 12/2004 | Besson ......................... 378/62 |
| 2005/0018888 A1 | * | 1/2005 | Zonneveld ................... 382/128 |
| 2005/0084069 A1 | * | 4/2005 | Du et al. .................... 378/98.9 |

OTHER PUBLICATIONS

Virtual Endoscopic Visualization of the Colon by Shape—Scale Signatures, Nappi et al., Mar.2005, IEEE Transactions on Information Technology in Biomedicine, vol. 9, No. 1.*
A Statistical 3-D Pattern Processing Method for Computer-Aided Detection of Polyps in CT Colonography, Gokturk et al., Dec. 2001, IEEE Transactions on Medical Imaging. vol. 20, No. 12.*
F. Rashid-Farrokhi et al., Local Tomography in Fan-Beam Geometry Using Wavelets, IEEE, 1996, 0-7803-3258-X/96, pp. 709-712.

* cited by examiner

*Primary Examiner*—Courtney Thomas
*Assistant Examiner*—Alexander Taningco
(74) *Attorney, Agent, or Firm*—Ziolkowski Patent Solutions Group, SC

(57) ABSTRACT

A method and system of CT colonography is presented that includes the acquisition of energy sensitive or energy-discriminating CT data from a colorectal region of a subject. CT data is acquired and decomposed into basis material density maps and used to differentiate and enhance contrast between tissues in the colorectal region. The invention is particularly applicable with the detection of colon polyps without cathartic preparation or insufflation of the colorectal region. The invention is further directed to the automatic detection of colon polyps.

24 Claims, 3 Drawing Sheets

CT COLONOGRAPHY SYSTEM

BACKGROUND OF THE INVENTION

The present invention relates generally to radiographic imaging and, more particularly, to a method and system of detecting colon polyps in a colorectal region of a subject without cathartic preparation or insufflation of the colorectal region. The present invention is particularly applicable with photon counting and/or energy discriminating CT systems.

Colorectal cancer is a leading cause of cancer deaths. There are several accepted screening techniques that have been developed for the detection of potentially cancerous polyps. It is widely recognized that if these polyps can be detected and removed, the incidence and mortality rates of colorectal cancer may be reduced.

Endoscopic colonoscopy is a common technique employed to detect potentially cancerous polyps. Colonoscopy, however, is an invasive and frequently uncomfortable experience for a patient. Recently, other techniques such as CT colonography, in which the principles of computed tomography is used to image the entire colon or colorectal region of a patient, have been developed and shown to be highly sensitive in the detection of these potentially cancerous polyps. While a CT colonography exam is considered much less invasive than a colonoscopy, CT colonography requires a cathartic bowel preparation, stool marker, and/or insufflation of the colon to capture contrast between polyps and stool in an image. While most patients do not experience complications from this cathartic preparation, the procedure can be highly disagreeable and is noted as a significant factor for patient non-compliance with screening regimens.

Furthermore, insufficient preparation can lead to fluid or stool retention which can obscure findings. As a result, it has been recommended that two exams be taken: one in the supine position and one in the prone position. Acquiring CT data when a patient is in the prone position allows for any residual fluid to collect at the bottom and allow a radiologist to uncover any polyps that may have been masked by the fluid when the patient was in the supine position. While taking two examines improves overall detection rates, it increases scan times and decreases patient throughput.

It would therefore be desirable to design a CT system capable of imaging a colorectal region of a subject with contrast between polyps and stool without cathartic preparation or insufflation thereof.

BRIEF DESCRIPTION OF THE INVENTION

The present invention is a directed method and apparatus for CT colonography that overcomes the aforementioned drawbacks. The present invention includes a method and system capable of collecting and characterizing the energy of radiation received by a radiation detector either through the use of an energy selective detector or through modulating the energy range of the x-ray tube source to identify colon polyps non-invasively and without cathartic preparation or insufflation of a colorectal region of a subject.

The present invention is applicable with a photon counting (PC) radiographic system having a radiation energy detector configured to detect radiation energy at a given flux rate and output signals indicative of the detected radiation energy. A shaper unit with a given shaping time is connected to receive the electrical signals and conditions them to provide electrical pulses indicative of the radiation photon energy. A PC channel is connected to receive the electrical signals and sample the electrical pulse signals of a certain height or intensity indicative of the photon energy by an adjustable pulse height discriminator or threshold. The PC channel is further configured to provide a photon count output over a sampling interval. The system also includes a control operationally connected to the PC channel and configured to automatically adjust the shaping time at least as a function of the given flux rate. The system also includes a control operationally connected to the PC channel and configured to automatically adjust the sensitivity to pulse height or threshold discriminator as a function of the given flux rate or shaping time.

The present invention is also applicable with an integrating energy selective detector, where the received radiation is registered in two or more energy ranges that may overlap through the use of either direct or indirect conversion detector materials using a layered design or depth of interaction to differentiate the energy bins.

The present invention is also applicable with a energy integration detector and an x-ray source modulated to adjust the spectra for two or more different energy functions.

Therefore, in accordance with one aspect of the present invention, an imaging scanner is disclosed and includes a radiation source and a radiation detector. The computer is operationally connected to the radiation detector and programmed to process x-ray projection data acquired by the radiation detector representing a first dataset and a second dataset. The first dataset is comprised of data at an energy level different than that of the second dataset. The computer may then decompose the two sets of energy projection data into two or more sets of projection data representing the projection due a first basis material and a second basis material. The projection of the basis material datasets may then be reconstructed to form basis material density maps and used to dataset to delineate composition of a colorectal region of a subject.

In accordance with another aspect of the present invention, a method of CT imaging includes acquiring energy sensitive CT data from an ROI of a subject. The method further includes decomposing the energy sensitive CT data into a first energy bin and a second energy bin and encoding pixels corresponding to data from the first energy bin dissimilarly than pixels corresponding to data from the second energy bin to capture contrast in an image of the ROI.

The present invention is also embodied in a computer program stored on a computer readable storage medium. The computer program includes a set of instructions that when executed by a computer causes the computer to receive energy sensitive CT data acquired from a colorectal region of a subject and decompose the energy discriminating CT data into at least two datasets. The computer is also caused to assign an encoding value to each dataset and reconstruct an image of the colorectal region with contrast between normal and abnormal tissue of a colorectal region without cathartic preparation of the colorectal region.

According to another aspect, the present invention includes a CT system having a radiation source and a radiation detector. The CT system further includes a computer programmed to receive data in a first energy spectrum acquired from a colorectal region of a subject and receive data in a second energy spectrum acquired from a colorectal region of a subject. The computer is further programmed to reconstruct an image of the colorectal region of a subject with contrast between normal and abnormal tissue of a colorectal region without cathartic preparation of the colorectal region.

In accordance with yet a further aspect of the present invention, a CT system is disclosed and includes a radiation source, a radiation detector, and a computer programmed to receive data in a first energy spectrum acquired from a colorectal region of a subject and receive data in a second energy spectrum acquired from the colorectal region of the subject. The computer is further programmed to detect and label intravenous or orally administered contrast agent in the colorectal region from the received data.

According yet a further aspect of the present invention, a CT system includes a radiation source as well as a radiation detector. A computer is included and programmed to receive data regarding a first energy spectrum acquired from the colorectal region of a subject as well as receive data regarding a second energy spectrum acquired from the colorectal region of the subject. The computer is also programmed to automatically characterize tissue as cancerous and non-cancerous based upon the received data.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other radiation energy sources.

Figure 1:
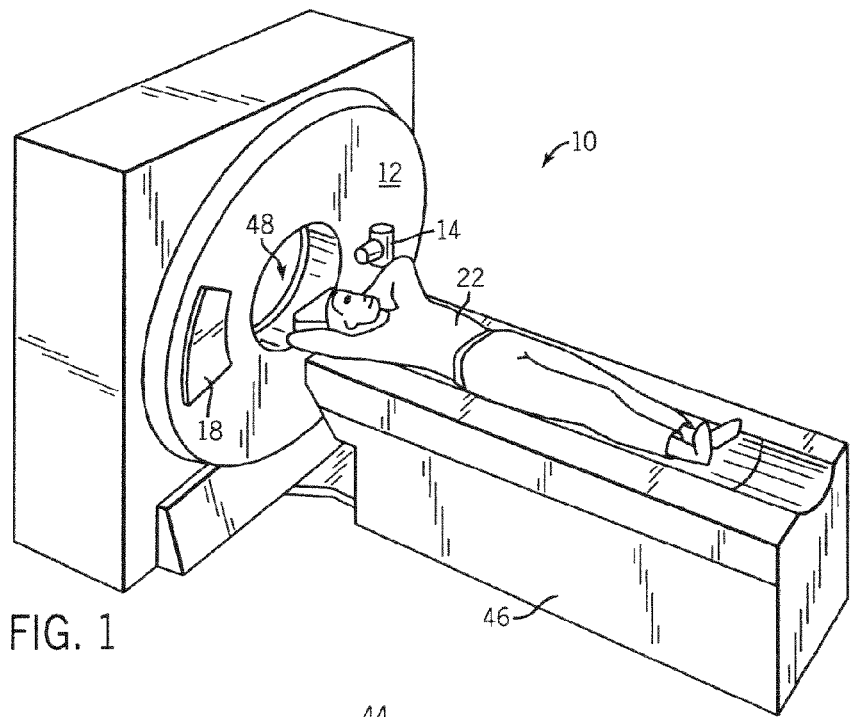
FIG. 1 is a pictorial view of a CT imaging system.
Figure 2:
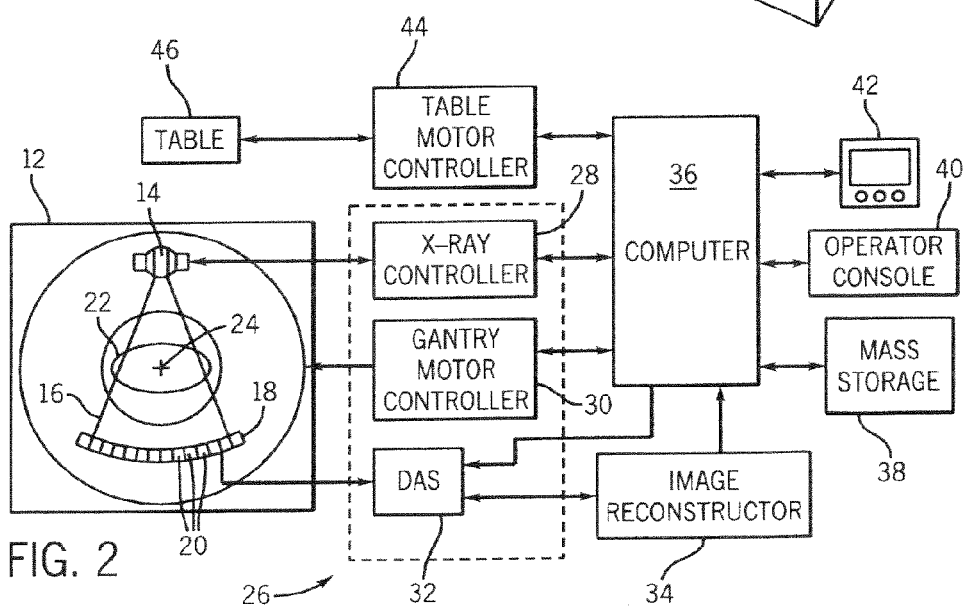
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly 18 on the opposite side of the gantry 12. Detector assembly 18 is formed by a plurality of detectors 20 which together sense the projected x-rays that pass through a medical patient 22. Each detector 20 produces an electrical signal that represents not only the intensity of an impinging x-ray beam but is also capable of providing photon or x-ray count data and energy level, and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 reviews data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated display screen 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

In one embodiment, CT system 10 is an energy-discriminating computed tomography (EDCT) system and is configured to be responsive to different incident x-ray spectra. This can be accomplished by acquiring projection data sequentially using different x-ray tube voltages. For example, two scans are acquired either back to back or interleaved in which the tube operates at 80 kVp and 160 kVp potentials, for example, generating a low and high energy spectrum respectively. Alternatively, special filters are placed between x-ray source 14 and the subject 22 such that detector rows collect projections of different x-ray energy spectrum either sequentially or interleaved. Yet another embodiment is to use energy sensitive photon counting detectors such that each x-ray photon reaching the detector is recorded with its photon energy. Yet another embodiment is to use energy sensitive detectors such that direct or indirect conversion material is used to separate photons into two or more energy bins that may overlap through the use of detector layers or depth of interaction detectors.

EDCT can lessen or eliminate problems, such as lack of energy discrimination or material characterization, associated with some CT systems altogether. In the absence of object scatter, ECT system 10 may be used to separately detect two regions of the incident photon energy spectrum, the low energy and the high energy portions of the incident x-ray spectrum. The behavior at any other energy can be derived based on the signal from the two energy regions. This phenomenon is driven by the fundamental fact that in the energy region where CT is interested, two physical processes dominate the x-ray attenuation: (1) Compton scatter and (2) the Photoelectric effect. In order to characterize the behavior of an object causing attenuation of the x-ray beam, two independent parameters are measured. Thus, detected signals from the two energy regions provide sufficient information to resolve the energy dependence of the object being imaged; hence, the composition of the material can be characterized.

The data analysis used in EDCT includes Compton and photoelectric decomposition and/or Basis material decomposition (BMD). In Compton and photoelectric decomposition, a pair of images is generated, which separately presents the attenuation from the Compton and photoelectric processes—instead of obtaining one image characterizing the overall attenuation coefficient in the reconstructed CT image. Also, a slight modification in the processing allows the generation of images representing density and effective atomic number. The BMD method is based on the concept that the x-ray attenuation of any given material in the energy range can be represented by a linear combination of a density mixture of other two known materials. These two materials are called the Basis Materials. Using BMD, two reconstructed images are obtained, each image representing the equivalent density of one of the basis materials. Since density is independent of x-ray photon energy, these images are relatively free of beam hardening artifacts. Additionally, the basis material is chosen to target a material of interest, thus enhancing the image contrast.

It should be noted that in order to optimize a multi-energy CT system not implementing energy discrimination with photon counting, the larger the energy separation in the x-ray spectra, the better the image quality. Also, the photon statistics in these two energy regions should be comparable, otherwise the energy region with reduced statistical information will dominate the noise in the reconstructed image.

There are different methods to obtain dual energy measurements: (1) scan with two distinctive energy spectra, (2) detect photon energy according to penetration depth at the detector, or (3) photon counting with energy discrimination. Photon counting provides clean spectra separation and an adjustable energy separation threshold for balancing photon statistics.

While applicable with each of the aforementioned methods, the present invention will be further described with respect to a multi-energy system having energy discriminating radiation detectors capable of counting photon events and associating an energy level to a counted event. To combat saturation of these detectors, a number of saturation techniques may be used. One such technique is described below.

Generally, high-sensitivity photon counting radiation detectors are constructed to have a relatively low dynamic range. This is generally considered acceptable for photon counting detector applications since high flux conditions typically do not occur. In CT detector designs, low flux detector readings through the subject are typically accompanied by areas of high irradiation in air, and/or within the contours of the scan subject requiring CT detectors to have very large dynamic range responses. Moreover, the exact measurement of photons in these high-flux regions is less critical than that for low-flux areas where each photon contributes an integral part to the total collected photon statistics. Notwithstanding that the higher flux areas may be of less clinical or diagnostic value, images reconstructed with over-ranging or saturated detector channel data can be prone to artifacts. As such, the handling of high-flux conditions is also important.

An x-ray flux management control is designed to prevent saturation of PC x-ray systems having detector channels characterized by low dynamic range. Dynamic range of a detector channel defines the range of x-ray flux levels that the detector channel can handle to provide meaningful data at the low-flux end and not experience over-ranging or saturating at the high flux end. Notwithstanding the need to prevent over-ranging and to provide diagnostically valuable data, the handling of low-flux conditions, which commonly occur during imaging through thicker cross-sections and other areas of limited x-ray transmission, is also critical in detector design. As such, the x-ray flux management control described herein is designed to satisfy both high flux and low flux conditions.

Generally, operation of a photon counting detector is characterized by a shaping time curve that is fixed. The shaping time curve defines a relationship or balance between charge integration time (single-event signal level) and detector channel recovery time so as to provide acceptable PC count-rates, noise suppression, and energy resolution. Typically, the detector channel is constructed to have a shaping time that favors low-flux rate conditions. That is, for low-flux rate conditions, which translate to fewer x-ray photons, a longer shaping time is preferred so that the entire photon charge cloud is integrated and SNR is optimized. There is generally relatively little constraint on the time necessary to integrate the entire photon cloud. Since the condition is characterized by low-flux, the detector channel is not likely to saturate while integrating or otherwise sampling the entire photon cloud. On the other hand, the low-flux rate favored, fixed time shaping may be insufficient for high-flux rate conditions. Moreover, if the time shaping is fixed to match or correspond to high-flux rate conditions, a negative impact on SNR and energy resolution during low-flux rate conditions follows.

Figure 3:
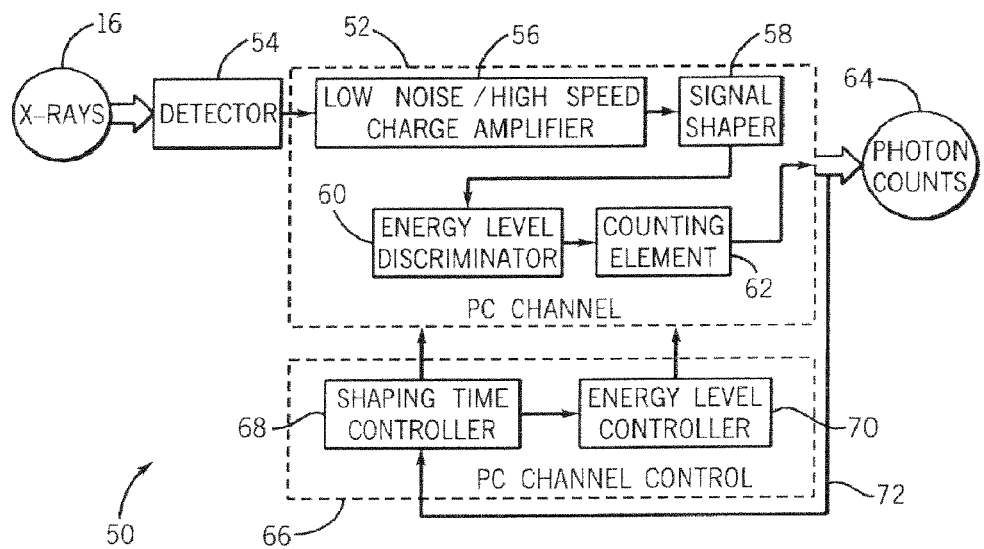
FIG. 3 is a block schematic diagram of a detector assembly according to the present invention.

Accordingly, the CT system is designed to dynamically and automatically control the shaping time of a detector channel such that low-flux as well as high-flux rate conditions are optimally addressed. Referring now to FIG. 3, a block schematic diagram of an x-ray detection system 50 applicable with the present invention is shown. System 50 includes a PC channel 52 connected to receive electrical signals from a detector element 54. Detector 54 is constructed to detect x-rays 16 projected by an x-ray source and attenuated by a subject, such as a medical patient. It is understood that the present invention is applicable with gamma rays and other forms of radiographic energy.

PC channel 52 includes a low-noise/high-speed charge amplifier 56 connected to receive the electrical signals from detector element 54. The amplified output of amplifier 56 is then input to a signal shaper 58 constructed to extract individual photon events from the electrical signals. Energy level discriminator 60 is connected to signal shaper 58 and is designed to filter photons based on their pulse height energy level relative to one or more thresholds. To this end, those photons having energy levels outside a desired range are excluded from counting and processing for image reconstruction. Minimally, discriminator 60 is designed to exclude those photons having an energy level corresponding to noise in the system. It is contemplated that multiple thresholds may be used to define energy level ranges. Counting element 62 receives those photons not filtered out by energy level discriminator 60 and is constructed to count the number of photons received at the detector and provide a corresponding output 64. As will be described and in contrast to known PC channels, operation PC channel 52 is governed by a variable shaping time.

PC channel 52 is operationally connected to a control 66 that includes a shaping time controller 68 and, preferably, an energy level controller 70. While it is preferred that control 66 include energy level controller 70, it is contemplated that the present invention may be carried out without it. In one embodiment, PC channel 52 includes an active filter whose operation defines the channel's shaping time. In this regard, resistive and capacitive characteristics of the active filter can be adjusted to manipulate the channel's shaping time properties.

Shaping time controller 68 is connected to PC channel 52 and is designed to adjust the shaping time characteristics of PC channel 52 based on photon count feedback received across feedback loop 72. More particularly, shaping time controller 68 increases the channel's shaping time when the detector element is exposed to low x-ray flux as measured by the number of photons counted 64. In contrast, when the x-ray flux on the detector element 54 increases, the time shaping controller decreases the time shaping or sampling window of PC channel 52.

As such, when the detector is experiencing higher x-ray flux, the amount of time the PC channel spends sampling the photon charge cloud is reduced. Accordingly, less precise photon and energy discriminatory data with respect to the photon charge cloud is determined; however, the channel recovers at a rate sufficient to avoid over-ranging. In this regard, as the shaping time or sampling window is caused to decrease, more photons are inspected for data, i.e. counted, while each detected photon provides less precise energy discriminatory information. And, under high flux conditions, each individual photon assumes less importance and the overall system performance and image quality is minimally impacted by the reduced SNR. On the other hand, when the detector is experiencing lower x-ray flux, the amount of time the PC channel spends to sample the photon charge cloud is lengthened which allows sufficient time to sample the entire photon charge cloud and attain relatively precise photon count and energy discriminatory data.

As referenced above, control 66 includes, in one embodiment, an energy level controller 70. Since the measured photon signal levels vary with channel shaping time, automatic energy discriminator energy level controller 70 is coupled to shaping time controller 68 and PC channel 52 to adjust or otherwise calibrate the energy level threshold of the PC channel in response to an adjustment in the shaping time. By performing appropriate channel calibration, photons having an acceptable or decreased energy level are counted to assure linear energy response independent of channel shaping time and count rate.

Figure 4:
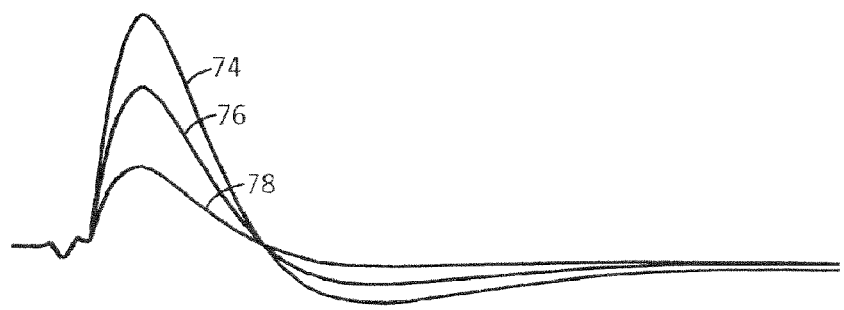
FIG. 4 is a graph illustrating signal amplitude plots for a number of shaping times for an exemplary PC detector.

Referring now to FIG. 4, a number of amplitude plots for several shaping time curves for an exemplary PC channel are illustrated. Decreasing the shaping time increases the potential count rate but, as shown, decreases the signal amplitude and increases noise. Specifically, adjusting the time shaping defined by curve 74 to that defined by curve 76 increases the potential count rate, but causes an inversely related decline in collective signal strength of the counted photons and negatively affects SNR. A further decrease in shaping time, i.e. curve 76 to curve 78 results in a further increase in count rate potential, but with additional decline in signal strength and SNR.

The present invention is further directed to CT colonography with the capturing of contrast between polyps and stool in a colorectal region of a patient using energy-discriminating CT data acquired with a CT system such as that described with respect to FIGS. 1–4. As described above, it is critical to prevent saturation or over-ranging of energy discriminating detectors at high x-ray flux conditions such that the output of a given radiation detector may be used for image reconstruction. Heretofore, a variable shaping time controller has been described to prevent over-ranging of a radiation detector. However, it is contemplated that the present invention is applicable with CT systems incorporating other techniques and mechanisms to prevent over-ranging of radiation detectors under high flux conditions including, but not limited to, dynamic collimation, dynamic two-current control, and variable shaped bowtie filters. In this regard, the energy sensitive or discriminating CT data avoids the inherent uncertainty of CT data acquired with a conventional CT system. That is, it is well known that different materials or mixtures of materials having different attenuation properties can produce the same CT or Houndsfield number if the density values are different such that the product of attenuation and density in the differing materials are equal. That is, the CT number for a given image voxel is a function of the number of photons impinged upon the radiation detector as well as the energy level of the x-rays received.

In contrast, the CT system described herein is capable of counting the number of photons received as well as determining an energy level for each received or counted photon. As will be described in greater detail below, it is possible from the photon count as well as the energy level of a counted photon to determine not only the density of an imaged material as well as the type of material imaged. This information can then be used to distinguish between stool and polyps or between contrast agent such as an intravenously administered Iodine and/or orally administered Barium Sulfate agent, and other tissues of similar CT number characteristics. One skilled in the art will appreciate that intravenous Iodine goes to the polyps or the colon wall whereas orally administered Barium Sulfate goes to the stool. The present invention is applicable with each and may be used to distinguish between unenhanced tissues and contrast enhanced tissues. Further, the present invention may be used to distinguish between different contrast agents delivered to different sites or tissues.

Figure 5:
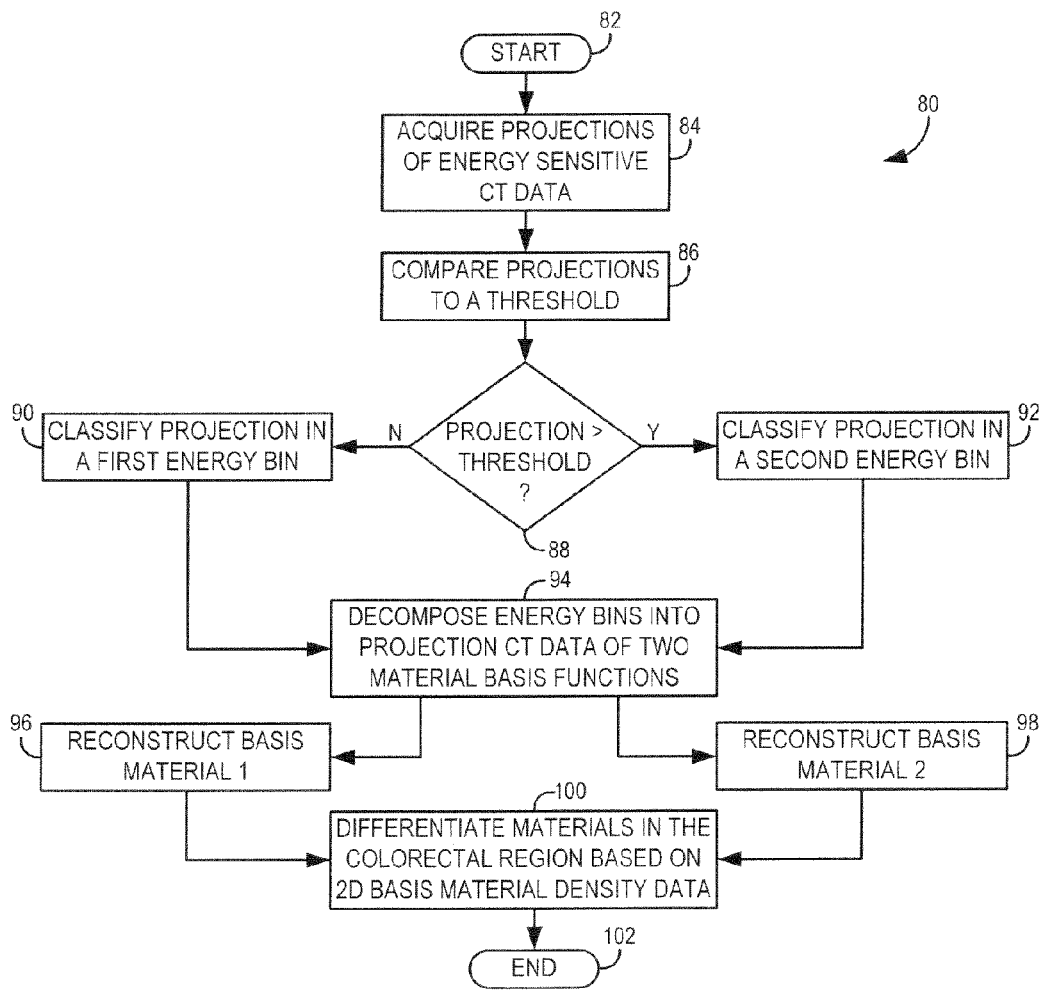
FIG. 5 is a flowchart setting forth steps of a CT colonography exam according to the present invention.

Referring now to FIG. 5, the steps of a colonography imaging process in accordance with one embodiment of the present invention will be described. The process 80 begins at 82 with the prescription of a CT exam to acquire CT data from a colorectal region of a patient. A CT scan is then administered at 84 consistent with the parameters established at 82 to acquire projections of energy sensitive CT data. As described above, energy sensitive CT data includes photon count as well as energy level information. As the acquired CT data includes photon counts as well as energy level information, the present invention contemplates a comparison of a projection to a threshold at 86 so as to bin the projection data into one or more energy bins. As such, projection is compared to a threshold at 88. Depending upon where the projection falls with respect to the threshold, the projection will be classified in either a first energy bin 90 or a second energy bin 92. In one contemplated example, the energy bins correspond to data acquired from contrast agent versus data acquired from water. While only two energy bins are illustrated in FIG. 5, it is contemplated that more than two energy bins or classifications may be applied in decomposing the energy sensitive CT data. It is also contemplated, as described above, that two or more energy bins may be acquired through other mechanisms, such as the use of modulating the energy spectra of the x-ray tube either through the adjustment of the peak voltage (kVp) or through the use of special filter materials.

Once the energy bins are computed, the energy bins are decomposed into projection CT data representing two basis materials 94. The two projection data sets are processed to form a reconstructed image of the density value of the first material 96 and a second material 98. It is contemplated that in lieu of decomposing the energy bins into two basis materials, the energy bins can be decomposed into another set of orthogonal basis functions, such as: effective atomic number and density, or photoelectric and Compton scattering components. Once the basis material density values are available, the two dimensional information can be used to differentiate the materials found in the colorectal region base on the two dimensional basis material density data 100. The two dimensional data has more information than the one dimensional data that is available from a conventional CT processing technique. Furthermore, the decomposition technique can separate materials that have the same CT number but a different representation in the basis material two-dimensional map due to different chemical compositions. In, this regard, more contrast between materials is generated using the material basis decomposition. The process is then completed at 102 with displaying of the image for evaluation by a radiologist or other health care provider. The display of the image can include additional post-processing of the data to generate a color-coded image that highlights materials of specific chemical compositions.

In the example illustrated above, the energy bins are designed to segment data corresponding to water from data corresponding to orally administered contrast agent. In this regard, the corresponding projections will be reconstructed to form images that represent the density of the contrast agent administered as well as the density of the water present in the image. As such, areas in the image that are infused with contrast agent will be differentiated from normal tissue more easily than relying on CT number density alone. Further, different tissues can be classified and separated, and ultimately differentially weighted such that tissue differentiation within the image is more readily ascertainable even though the CT number associated with the tissues and/or contrast agent is equal. In this regard, each pixel in a reconstructed image may be encoded with a value that during image reconstruction is used to differentiate that imaged in a given pixel from that imaged in another pixel. It is also contemplated that rather than a composite image, an image of only colon polyps may be reconstructed. That is, based on the tissue differentials consistent with the photon count and energy discriminating data, data corresponding to colon polyps can be isolated and used for image reconstruction while all non-polyp data is set to a background level.

Figure 6:
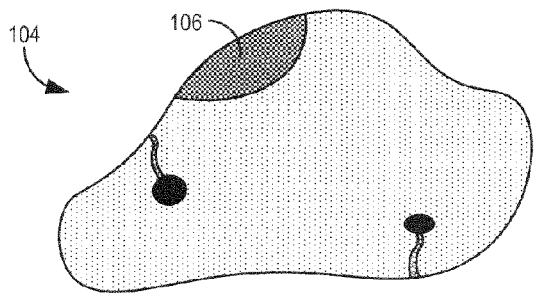
FIG. 6 is a schematic view of a colorectal region of a subject having polyps disposed therein.

Referring now to FIG. 6, a colorectal region of a subject is schematically illustrated as including a polyp 106 surrounded by stool 108 in the colorectal region 104. In a preferred embodiment, the colorectal region is not insufflated or subjected to cathartic preparation prior to CT data acquisition. It is contemplated, however, the a contrast agent such as an intravenously administered Iodine or orally administered Barium Sulfate may be used to further capture contrast between colon polyps that may be potentially cancerous from normal tissue within the colorectal region. As is well known, a contrast agent may be selected that is easily absorbed by cancerous cells but not other tissues within the colorectal region. As such, cancerous or other pathological abnormalities within the colorectal region may develop pools of contrast agent that can be used to identify a potentially cancerous colon polyp. In this regard, through the acquisition and decomposing of energy sensitive and/or energy discriminating CT data, it is possible to identify, automatically, a malignant polyp within the colorectal region. That is, the material basis density values can indicate that contrast agent targeted to cancerous cells is present in the polyp as opposed to naturally occurring tissue that may have similar CT number. For example, the material basis values may be compared to a lookup table of empirical data and based on that comparison can be identified as a colon polyp or stool. Additionally, by comparing material density values to a neighboring values in a reconstructed image, it is possible to determine the size as well as shape of an identified or detected colon polyp. In this regard, it is possible to implement detection processes to use the CT number, shape, texture, and material composition of a selected portion of a reconstructed image to automatically detect and characterize colon polyps.

Therefore, the present invention includes an imaging scanner. The imaging scanner includes a radiation source and a radiation detector. The computer is operationally connected to the radiation detector and programmed to decompose CT data acquired by the radiation detector into a first dataset and a second dataset to delineate composition of a colorectal region of a subject. The first dataset is comprised of data at an energy level different than that of the second dataset.

A CT system is present and acquires energy sensitive CT data from an ROI of a subject. The method further includes decomposing the energy sensitive CT data into a first energy bin and a second energy bin and encoding pixels corresponding to data from the first energy bin dissimilarly than pixels corresponding to data from the second energy bin to capture contrast in an image of the ROI.

The present invention further includes a computer program stored on a computer readable storage medium. The computer program includes a set of instructions that when executed by a computer causes the computer to receive energy-discriminating CT data acquired from a colorectal region of a subject and decompose the energy-discriminating CT data into at least two datasets. The computer is also caused to assign an encoding value to each dataset and reconstruct an image of the colorectal region with contrast between normal and abnormal tissue of a colorectal region without insufflation of the colorectal region.

Additionally, the present invention includes a CT system having a radiation source and a radiation detector. The CT system further includes a computer programmed to receive data in a first energy spectrum acquired from a colorectal region of a subject and receive data in a second energy spectrum acquired from a colorectal region of a subject. The computer is further programmed to reconstruct an image of the colorectal region of a subject with contrast between data within the first energy spectrum and data within the second energy spectrum.

Further, in accordance with the present invention, a CT system is disclosed and includes a radiation source, a radiation detector, and a computer programmed to receive data in a first energy spectrum acquired from a colorectal region of a subject and receive data in a second energy spectrum acquired from the colorectal region of the subject. The computer is further programmed detect a labeled contrast agent in the colorectal region from the decomposed data.

The present invention further includes a CT system having a radiation source as well as a radiation detector. A computer is included and programmed to receive data regarding a first energy spectrum acquired from the colorectal region of a subject as well as receive data regarding a second energy spectrum acquired from the colorectal region of the subject. The computer is programmed to decompose the energy sensitive data into material basis function data. The computer is also programmed to automatically characterize tissue as cancerous and non-cancerous based upon the received data.

The present invention has been described in terms of the preferred embodiment, and it is recognized that equivalents, alternatives, and modifications, aside from those expressly stated, are possible and within the scope of the appending claims.

What is claimed is:

1. An imaging scanner comprising:
    a radiation source;
    a radiation detector; and
    a computer programmed to decompose CT data acquired by the radiation detector into a first dataset and a second dataset to delineate composition of a colorectal region of a subject, the colorectal region having an intravenously administered contrast agent positioned in a polyp attached to a colon wall, wherein the first dataset is comprised of data at an energy level different than that of the second dataset.

2. The imaging scanner of claim 1 wherein the computer is further programmed to reconstruct an image of the colorectal region of the subject with contrast between stool and polyps.

3. The imaging scanner of claim 2 wherein the computer is further programmed to display the image with color-coded differentiation between the stool and the polyps.

4. The imaging scanner of claim 1 wherein the computer is further programmed to decompose the CT data such that the first dataset is comprised of data corresponding to water and the second dataset is comprised of data corresponding to contrast agent.

5. The imaging scanner of claim 1 wherein the computer is further programmed to automatically determine presence of colon polyps in the colorectal region of the subject from the decomposed CT data.

6. The imaging scanner of claim 5 wherein the computer is further programmed to compare a material basis density pair to a look-up table and, from the comparison, determine if that imaged corresponds to a colon polyp.

7. The imaging scanner of claim 6 wherein the computer is further programmed to image the colorectal region of the subject with colon polyp detection without cathartic preparation or insufflation of the colorectal region of the subject.

8. A method of CT imaging comprising the steps of:
    acquiring energy sensitive CT data from an ROI of a subject;
    decomposing the energy sensitive CT data into a first energy bin and a second energy bin, wherein the first energy bin is segmented to represent a density of a contrast agent intravenously administered and the second energy bin is segmented to represent a density of water; and
    encoding pixels corresponding to data from the first energy bin dissimilarly than pixels corresponding to data from the second energy bin to enhance contrast in an image of the ROI.

9. The method of claim 8 wherein the ROI includes a colorectal region of the subject and further comprising the step of introducing a contrast agent into the ROI.

10. The method of claim 8 further comprising the step of imaging the ROI without cathartic preparation or insufflation of the ROI.

11. The method of claim 8 further comprising the step of decomposing the energy sensitive CT data into a first energy bin comprised of data corresponding to water and a second energy bin comprised of data corresponding to contrast agent.

12. The method of claim 11 further comprising the step of reconstructing an image of the ROI with color-coded differentiation between data of differentiated materials.

13. The method of claim 8 further comprising the step of reconstructing a single image comprised of data from a CT image and two-dimensional basis material data.

14. A computer readable storage medium having a computer program stored thereon and representing a set of instructions that when executed by a computer causes the computer to:
    receive energy sensitive CT data acquired from a colorectal region of a subject;
    decompose the energy sensitive CT data into at least two datasets;
    assign an encoding value to each dataset; and
    reconstruct an image of the colorectal region with contrast between stool and abnormal tissue of the colorectal region without insufflation of the colorectal region, the abnormal tissue having a first contrast agent therein, and the stool having a second contrast agent therein.

15. The computer readable storage medium of claim 14 wherein the computer is further caused to color-code the image to enhance contrast between materials of the colorectal region.

16. The computer readable storage medium of claim 14 wherein the computer is further caused to automatically determine colon polyps in the colorectal region.

17. The computer readable storage medium of claim 16 wherein the computer is further caused to compare material basis data from the energy sensitive CT data to a threshold and, based on the comparison, determine colon polyp presence in the colorectal region.

18. The computer readable storage medium of claim 14 wherein the computer is further programmed to decompose the energy sensitive CT data into datasets representing two basis materials.

19. The computer readable storage medium of claim 18 wherein the contrast agent dataset includes data acquired from a intravenous or orally administered contrast agent into the colorectal region of the subject.

20. A CT system comprising:
    a radiation source;
    a radiation detector; and
    a computer programmed to:
    receive data in a first energy spectrum acquired from a colorectal region of a subject, the colorectal region comprising stool, polyps, and a colon wall wherein iodine is an intravenously administered contrast agent in one of the polyps and the colon wall;
    receive data in a second energy spectrum acquired from the colorectal region of the subject; and
    reconstruct an image of the colorectal region of the subject with contrast between data in the first energy spectrum and data in the second energy spectrum.

21. A CT system comprising:
    a radiation source;
    a radiation detector; and
    a computer programmed to:
    receive data in a first energy spectrum acquired from a colorectal region of a subject;
    receive data in a second energy spectrum acquired from the colorectal region of the subject; and
    detect a labeled, intravenously administered contrast agent delivered to an abnormal tissue of the colorectal region from the received data.

22. A CT system comprising:
    a radiation source;
    a radiation detector; and
    a computer programmed to:
    receive data regarding a first energy spectrum acquired from a colorectal region of a subject;
    receive data regarding a second energy spectrum acquired from the colorectal region of the subject; and automatically characterize tissue as cancerous and non-cancerous based upon the received data.

23. A method of CT imaging comprising the steps of:
acquiring energy sensitive CT data from an ROI of a subject, wherein the ROI includes a colorectal region of the subject;
introducing a contrast agent into the ROI;
decomposing the energy sensitive CT data into a first energy bin and a second energy bin; and
encoding pixels corresponding to data from the first energy bin dissimilarly than pixels corresponding to data from the second energy bin to enhance contrast in an image of the ROI.

24. A method of CT imaging comprising the steps of:
acquiring energy sensitive CT data from an ROI of a subject;
imaging the ROI without cathartic preparation or insufflation of the ROI;
decomposing the energy sensitive CT data into a first energy bin and a second energy bin; and
encoding pixels corresponding to data from the first energy bin dissimilarly than pixels corresponding to data from the second energy bin to enhance contrast in an image of the ROI.

* * * * *